US012303491B2

(12) United States Patent
Lebo et al.

(10) Patent No.: US 12,303,491 B2
(45) Date of Patent: May 20, 2025

(54) ECONAZOLE NITRATE MEDICAL PATCH AND METHODS OF USE THEREOF

(71) Applicant: Temple University-Of The Commonwealth System of Higher Education, Philadelphia, PA (US)

(72) Inventors: David B. Lebo, Warminster, PA (US); Cong Li, Philadelphia, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/488,250

(22) PCT Filed: Feb. 28, 2018

(86) PCT No.: PCT/US2018/020080
§ 371 (c)(1),
(2) Date: Aug. 23, 2019

(87) PCT Pub. No.: WO2018/160613
PCT Pub. Date: Sep. 7, 2018

(65) Prior Publication Data
US 2021/0212994 A1 Jul. 15, 2021

Related U.S. Application Data

(60) Provisional application No. 62/464,483, filed on Feb. 28, 2017.

(51) Int. Cl.
*A61K 31/4174* (2006.01)
*A61K 9/00* (2006.01)
*A61K 9/70* (2006.01)
*A61K 47/10* (2017.01)
*A61K 47/20* (2006.01)

(52) U.S. Cl.
CPC ........ *A61K 31/4174* (2013.01); *A61K 9/0014* (2013.01); *A61K 9/7061* (2013.01); *A61K 47/10* (2013.01); *A61K 47/20* (2013.01)

(58) Field of Classification Search
CPC ..... A61K 31/4174; A61K 47/20; A61K 47/10
See application file for complete search history.

(56) References Cited

U.S. PATENT DOCUMENTS

| 5,219,877 | A | * | 6/1993 | Shah | A61K 9/0014 |
| | | | | | 514/394 |
| 5,696,164 | A | * | 12/1997 | Sun | A61K 31/195 |
| | | | | | 514/562 |
| 6,159,977 | A | * | 12/2000 | Reeves | A61K 31/20 |
| | | | | | 514/723 |
| 6,846,837 | B2 | | 1/2005 | Maibach | |
| 2003/0235541 | A1 | * | 12/2003 | Maibach | A61K 47/26 |
| | | | | | 424/61 |
| 2007/0269379 | A1 | * | 11/2007 | Mitragotri | G01N 33/5082 |
| | | | | | 435/7.1 |
| 2009/0202602 | A1 | * | 8/2009 | Ishima | A61K 9/0014 |
| | | | | | 424/405 |
| 2018/0028466 | A1 | * | 2/2018 | Lee | A61P 9/10 |

OTHER PUBLICATIONS

Li (Dissertation entitled "The preformulation and formulation development for the transungual delivery of the antifungal drug econazole nitrate", Jul. 2015, pp. i-xx and pp. 1-159) (Year: 2015).*
Gungor et al (Plasticizers in Transdermal Drug Delivery Systems, InTech Open Science, 2012, 212 pages) (Year: 2012).*
Palliyil et al (International Journal of Pharma Medicine and Biological Sciences, 2014, vol. 3, pp. 152-164) (Year: 2014).*
Gungor et al (Intech Open Science, Mar. 21, 2012, chapter 5, pp. 91-112) (Year: 2012).*
Yang et (Journal of Laboratory Automation, 2012, vol. 17, pp. 50-58) (Year: 2012).*
Elkeeb R, AliKhan A, Elkeeb L, Hui X, Maibach HI. Transungual drug delivery: Current status. International Journal of Pharmaceutics. 2010;384(1-2):1-8.
Gunt, H. B. "Hydration effect on human nail permeability" Ph.D. Dissertation, University of Cincinnati, 2006 (167 pages).
Li, Cong, "A Preformulation Development Study for the Transungual Delivery of the Antifungal Drug Econazole Nitrate" M.S. Dissertation, Temple University, Jan. 2014 (73 pages).
Li, Cong, "The preformulation and formulation development for the transungual delivery of the antifungal drug econazole nitrate" Ph.D. Dissertation, Temple University, Jul. 2015 (179 pages).

* cited by examiner

*Primary Examiner* — Mark V Stevens
(74) *Attorney, Agent, or Firm* — Riverside Law LLP

(57) ABSTRACT

The invention provides an econazole nitrate and thiourea medical patch for the treatment of nail and skin onychomycosis, achieving improved drug penetration, and thus allowing more drug to penetrate into the nail bed and reach the minimum inhibitory concentration.

13 Claims, 5 Drawing Sheets

ECONAZOLE NITRATE MEDICAL PATCH AND METHODS OF USE THEREOF

CROSS-REFERENCE TO RELATED APPLICATIONS

The present application is a 35 U.S.C. § 371 national phase application from, and claiming priority to, International Application PCT/US2018/020080, filed Feb. 28, 2018, which claims priority under 35 U.S.C. § 119 (e) to U.S. Provisional Patent Application Ser. No. 62/464,483, filed Feb. 28, 2017, all of which are incorporated herein by reference in their entireties.

BACKGROUND OF THE INVENTION

Fungal infections of the nail, referred to by the terms "nail fungus," "onychomycosis," or "tinea unguium," are common throughout the world. An estimated 2-13% of the population is affected in North America, with at least 15-20% of those aged 40-60 having one or more fingernails or toenails infected. Toenails are much more commonly affected than fingernails. Infections can range from superficial, causing little more than discoloration, to severe, resulting in loss of the nail together with deformities of the surrounding digit. The incidence of onychomycosis has been rising over the past few decades, due to factors such as an increased elderly population, increased participation in vigorous physical activity while wearing moisture-retaining shoes and socks, an increase in the number of HIV infected individuals, an increased incidence of diabetes, and increased use of steroids, antibiotics, and other therapeutics that can suppress immunologic responses to fungi. While nail fungus is rarely life threatening, it causes significant pain, inconvenience, embarrassment, emotional distress, and limitations to manual performance and ambulation. Individuals with moderate to severe onychomycosis can lose their ability to perform many routine tasks (such as fastening buttons, picking up small objects, walking significant distances) and can lose the ability to perform satisfactorily in their occupations. Due to the unpleasant appearance of their hands or feet, these individuals may become socially self-conscious and embarrassed, and may avoid intimate or other close contact with people. Loss of self-esteem, anxiety, and depression commonly result from moderate to severe cases of fungal nail infection.

Onychomycosis is caused most commonly by several species of dermatophytes (parasitic fungi that infect the keratin-rich tissue of the stratum corneum, hair, and nails) and, less commonly, by nondermatophyte molds or by yeasts, primarily of the genus *Candida*. An estimated 90% of cases are caused by dermatophytes, primarily of the genera *Trichophyton, Microsporum,* and *Epidermophyton,* while about 8% are caused by nondermatophyte molds and 2% by yeasts. The causative agent in onychomycosis can rarely be determined by clinical appearance; microscopic examination or culturing is usually required. Furthermore, an infected nail colonized by one species can develop secondary infections by other fungi, yeasts, or bacteria. Onychomycosis can affect the nail plate, the nail bed (the tissue directly under the nail plate), the nail matrix or nail root (the thickened skin at the base of the nail from which the nail plate develops), the cuticle, the hyponychium (the thickened layer of epidermis beneath the free end of the nail), and the proximal and lateral nail folds (the skin adjacent to the base and sides of the nail).

Onychomycosis can be categorized into several varieties based on clinical appearance. Distal and lateral subungual onychomycosis (DLSO) is the most common variety. It usually results from a fungal infection of the skin (usually the plantar skin of the foot) spreading to the nail bed and then to the underside of the nail plate via the hyponychium. The distal and lateral parts of the nail plate become thickened, white, and opaque. In addition, the nail bed becomes hyperkeratotic and onycholysis (separation of the nail plate from the bed, ultimately resulting in loss of the nail) commonly ensues. Paronychia (inflammation of the tissues adjacent to the nail) is also common. *Trichophyton rubrum* is the most common pathogen. Endonyx onychomycosis (EO) is a variety of DLSO in which the fungus spreads directly from the skin to the nail plate rather than to the nail bed. The nail again is thickened, white, and opaque, but there is no evident nail bed hyperkeratosis or onycholysis. White superficial onychomycosis (WSO) variety is almost always found on toenails. The surface of an infected nail develops white dots or powdery patches and the nail becomes rough and crumbly. *Trichophyton mentagrophytes* (*T. interdigitale*) is the most common cause, though some nondermatophyte molds such as *Acremonium, Aspergillus,* and *Fusarium* can also infect the upper surface of the nail plate. The nondermatophyte molds commonly cause black or green nails. Proximal subungual onychomycosis (PSO) is the least common variety, in which the fungus first attacks the cuticle and proximal nail fold, and then penetrates the proximal nail plate. The distal part of the nail remains normal. *Candida* onychomycosis (CO), in which the yeast, nearly always *Candida albicans*, infects the nail folds (paronychia), the nail plate and surrounding tissues (in chronic mucocutaneous candidiasis), the nail bed, or any combination of these. The entire digit commonly becomes swollen and deformed. *Candida* may cause onycholysis or it may colonize onycholytic nails (resulting from trauma or another infection). *Candida* infection associated with paronychia is almost always secondary to trauma to the nail folds. Total dystrophic onychomycosis (TDO), in which the entire nail plate is thickened, yellow-brown, and opaque. All the adjacent tissues are affected, and the nail matrix may be permanently damaged, preventing normal nail growth even after the infection resolves. TDO can be the endpoint of any of the other onychomycosis varieties.

Onychomycosis is presently treated primarily with oral antifungal agents. Topical agents are rarely effective by themselves, except in mild cases that only affect the distal nail plate. They may, however, be beneficial in combination with oral therapy. In severe cases, the affected nail (and sometimes the nail bed and matrix) is removed surgically or by use of a urea containing formulation; removal of the nail is done in conjunction with oral and sometimes topical therapy. The preferred therapy for onychomycosis is orally administered treatment with terbinafine (Lamisil™), itraconazole (Sporanox™), or fluconazole (Diflucan™). Terbinafine, an allylamine, is active against dermatophytes, but has considerably less efficacy against nondermatophyte molds and against yeasts. Itraconazole and fluconazole are triazoles that are effective against dermatophytes, nondermatophyte molds, and yeasts. When administered daily, all of these compounds can cause hepatic injury, and monitoring of liver enzymes is required. Pulse therapy (typically, administration one week per month) reduces the risks for hepatic damage, but prolongs the course of therapy from about 6 to 12 weeks to at least several months. Topical antifungal treatments are now administered mainly in cases where the fungal infection is restricted to the distal half of the nail plate or in cases in which the patient cannot tolerate oral therapy. Their low efficacies appear due mainly to their inability to adequately penetrate the nail. Topical antifungal agents include allylamines (including terbinafine), triazoles (including itraconazole and fluconazole), imidazole derivatives (including ketoconazole, miconazole, clotrimazole, and enconazole), amorolfine, ciclopirox olamine, sodium pyrithione, bifonazole plus urea, and propylene glycol plus urea plus lactic acid. Examples of commercially available products include:

Eco-Nail nail lacquer, 5% econazole+18% SEPA nail lacquer. Promotes the release of econazole from dried lacquer film, creating a large chemical gradient at the lacquer-nail interface, to drive econazole into the deep nail plate. SEPA acts as a percutaneous penetration enhancer which itself has no effect on nail and do not penetrate nail. MacroChem Corporation.

Loceryl nail film, antifungal drug, amorolfine. A non-water soluble film of amorolfine formed on the nail plate and this film remains in place for 1 week. The film contains a high concentration of amorolfine and forms a deport from which the drug is delivered and which allow the drug penetrate the nail. Galderma Australian Pty Ltd.

Zalain nail patch, Sertaconazole nitrate. Once-a-week nail patch for treatment of onychomycosis & onychodystrophy. Labtec.

Penlac nail lacquer, Ciclopirox topical solution. Apply daily to treat onychomycosis, a broad-spectrum antifungal medication that also has antibacterial and anti-inflammatory properties. Dermik Laboratories Inc.

Jublia nail solution, 10% Efinaconazole. Recently FDA approved topical solution to treat nail fungus (onychomycosis). Valeant Pharmaceuticals.

Econazole nitrate (EN) is a representative of azole antifungals. Econazole nitrate is a topical antifungal agent that is currently indicated for a variety of fungal diseases, including tinea pedis, tinea cruris, tinea corporis, and cutaneous candidiasis, as well as for the treatment of *Tinea versicolor*. Econazole nitrate has shown activity against a variety of dermatophytes and yeasts, including most strains of *Epidermophyton floccosum, Microsporum audouinii, M. canis, M. gypseum, Trichophyton mentagrophytes, T. rubrum, T. tonsurans, Candida albicans*, and *Malassezia furfur*. Econazole nitrate is a leading antifungal used topically in the United States, with over 20 years of clinical use and history with an excellent safety profile.

Nails are skin appendages that are made of hard plates of keratinized epidermal cells over dorsal surfaces at the ends of fingers and toes and correspond to the stratum corneum in the skin. The stratum corneum of the skin is composed mainly of proteins with low sulfur contents, called soft keratins. By contrast, the nail is composed mainly of hard keratins with high sulfur contents and possesses properties as physico-chemically stable, poorly water-soluble proteins. Because the nail has a much lower lipid content than that of the stratum corneum of the skin, it exhibits a totally different behavior than skin in terms of drug absorption. The barrier properties of the nail plate and its thickness pose the greatest challenge towards permeation of any topically applied antifungal drug. Thus, there remains a need in the art for new and improved econazole formulations, and methods for use thereof against nail infections. This invention fulfils this need.

SUMMARY OF THE INVENTION

In one aspect, the invention relates to a pharmaceutical composition comprising an imidazole class drug and a permeability enhancer. In one embodiment, the imidazole class drug is econazole nitrate. In another embodiment, the permeability enhancer is thiourea. In another embodiment, the pharmaceutical composition further comprises propylene glycol. In another embodiment, the pharmaceutical composition further comprises a hydrophobic plasticizer. In another embodiment, the pharmaceutical composition further comprises triethyl citrate. In another embodiment, the pharmaceutical composition further comprises a pH adjuster. In another embodiment, the pharmaceutical composition further comprises polyvinylpyrrolidone. In another embodiment, the pharmaceutical composition further comprises an acrylate.

In another aspect, the invention relates to a medical patch comprising a backing membrane and a pharmaceutical composition of the invention.

In another aspect, the invention relates to a method for treating a fungal infection in a subject, comprising administering to the subject a pharmaceutically effective amount of a pharmaceutical composition of the invention. In one embodiment, the pharmaceutical composition is part of a medical patch. In another embodiment, the fungal infection is a nail fungal infection. In another embodiment, the fungal infection is onychomycosis. In another embodiment, the fungal infection affects a portion of the subject– skin. In another embodiment, the fungal infection affects at least one of subject's nail.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2A: neoprene nail adapters with orifice diameter of 3 mm, and FIG. 2B: Franz diffusion cell showing the donor compartment, receiver compartment and the nail adapter.

DETAILED DESCRIPTION OF THE INVENTION

Figure 1:
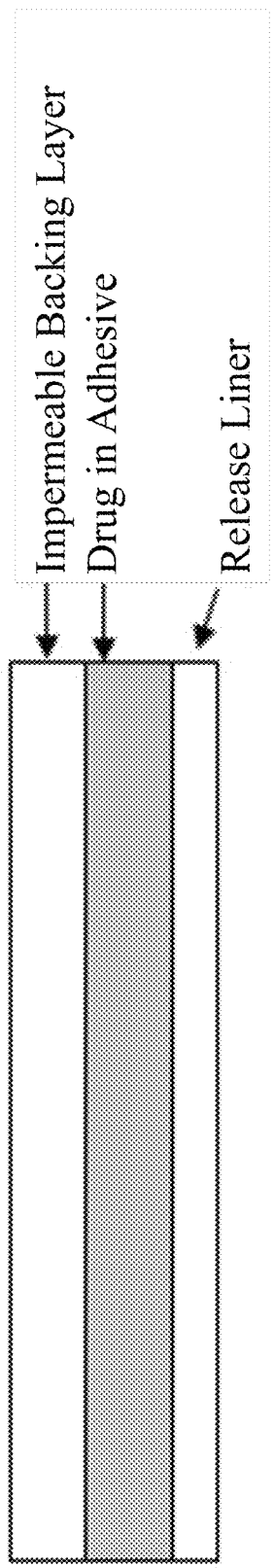
FIG. 1 is a schematic depicting the drug-in-adhesive (DIA) design of the transungual patch consisting of a backing membrane, econazole nitrate (EN) and permeability enhancer (PE) dissolved or dispersed in pressure sensitive adhesive, and release liner.

The present invention relates to the unexpected discovery that the antifungal drug econazole nitrate can successfully penetrate the human skin and nail from a formulation when accompanied by the appropriately selected penetration enhancer. The present invention further relates to a nail patch formulation containing the antifungal drug econazole nitrate and the penetration enhancer thiourea. The invention achieves improved drug nail penetration, and allows more drug to penetrate into the nail bed and reach the minimum inhibitory concentration in order to treat the nail fungus disease onychomycosis.

In one aspect, the invention relates to formulations, including a nail patch, comprising econazole nitrate, which is an imidazole class antifungal drug. Econazole nitrate is effective against a wide variety of fungi, and has been used topically to treat vaginal candidosis and other fungus infection disease, including nail fungus disease. The barrier properties of the nail plate and its thickness pose the greatest challenge towards permeation of any topically applied antifungal drug. Thus, in another aspect, the invention relates to the use of a penetration enhancer, which can improve drug permeation in a multitude of ways, including enhancement in solubility and/or acting on the barrier properties of the nail plate. In one aspect, the penetration enhancer in this patch is thiourea, which can break the disulphide bond of the keratin, and directly acts on the nail plate.

In one aspect, the invention relates to the use of a medical patch in a method to deliver drug to the nail plate. A nail patch is an occlusive bandage. In one aspect of the invention, upon application of the nail patch, the nail plate will be hydrated, which leads to increased permeation. In one aspect of the invention, the patch formulation presents a big advantage compared to a nail lacquer formulation for example, which dries out the nail. In one aspect, a skin permeation study and transungual permeation study have been performed to test the nail patch efficacy in the methods of the invention, using a patch without thiourea as control. The skin and transungual permeation study results showed that the nail patch with penetration enhancer thiourea is much more effective compared to the control.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in formulation science, cell culture, molecular genetics, organic chemistry, and peptide chemistry are those well-known and commonly employed in the art.

The articles "a" and "an" are used herein to refer to one or to more than one, i.e., to at least one of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "or," as used herein, means "and/or" unless explicitly indicated to refer to alternatives only or the alternatives are mutually exclusive, although the disclosure supports a definition that refers to only alternatives and "and/or."

The terms "inhibiting," "reducing," "preventing," "diminishing," and variations of these terms, as used herein include any measurable decrease, including complete or substantially complete inhibition.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "topical," as used herein, refers to the administration of the compositions of the invention to any exposed area of a subject's body. Application of a composition of the invention to nail(s), skin and underlying tissues, as well as administration to mucosa and underlying tissues, are all examples of topical administration.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disease, disorder or condition includes: (i) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disorder or condition, (ii) inhibiting the state, disease, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition associated with onychomycosis, including alleviating symptoms of such diseases.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Throughout this disclosure, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

Compositions of the Invention

In one aspect, the invention relates to compositions comprising an antifungal medication. In one embodiment, the antifungal medication is an imidazole class drug. In one embodiment, the antifungal medication is econazole nitrate. Econazole nitrate is an antifungal medication of the imidazole class. For local application the nitrate salt of econazole is used. In preliminary investigations of systemic use in a few patients econazole base has been administered orally or intravenously. In uncontrolled studies in large numbers of patients, econazole nitrate has been administered topically in the treatment of dermatomycoses because it is effective against a wide variety of fungi. It has also been used vaginally in the treatment of vaginal candidiasis. In dermatological studies about 90% of patients were cured, often after a relatively short treatment period (2 to 6 weeks). (Heel R et al, 1978).

TABLE 1

The Physicochemical Properties of Econazole Nitrate

| | |
|---|---|
| Molecular weight | 444.7 g/mol |
| Molecular formula | $C_{18}H_{16}Cl_3N_3O_4$ |
| Log P | 5.5 |
| pKa | 6.77 |
| Melting Point | 162° C. |
| Water Solubility | <0.1 g/100 mL at 19° C. |
| Description | White crystalline powder |
| Chemical Structure | |

Econazole, has in vitro activity against some Gram-positive cocci and bacilli, the minimum inhibitory concentrations for these organisms being similar to those for yeasts.

TABLE 2

The Minimum Inhibitory Concentration (MIC) of EN against bacteria

| | MIC (μg/ml) | | | |
|---|---|---|---|---|
| | econazole | | miconazole | |
| Bacteria | base | nitrate | base | nitrate |
| Staphylococcus aureus | 12.5 | 12.5 | 6.25 | 6.25 |
| Staphylococcus epidermidis | 12.5 | 12.5 | 6.25 | 6.25 |
| Streptococcus pyogenes | 12.5 | 12.5 | 6.25 | 6.25 |
| Streptococcus bovis | 6.25 | 6.25 | 3.12 | 3.12 |
| Streptococcus faecalis | 25 | 25 | 25 | 25 |
| Streptococcus faecium | 25 | 25 | 25 | 25 |
| Corynebacterium diphtheria | 0.78 | 0.78 | 0.39 | 0.39 |
| Listeria monocytogenes | 1.56 | 1.56 | 1.56 | 1.56 |
| Bacillus subtilis | 12.5 | 12.5 | 3.12 | 3.12 |

From the patients tested in pharmacokinetics studies it appears that about 90% of topically applied econazole nitrate (as a cream) remain on the skin surface, and occlusion only slightly increases the extent of absorption. Topical administration of econazole provides little systemic absorption. Following administration of econazole vaginal cream, less than 3% of the dose is recovered in urine and feces over 96 hours. The plasma protein binding of econazole is greater than 98%. The elimination half-life of econazole ranged from 4 to 6 hours in two patients with normal renal and hepatic function. Following administration of radio labeled econazole, 39% to 40% of the dose is excreted into the urine and 23% to 31% is recovered in the feces (probably as metabolites) over 5 days. No unchanged econazole is detected in urine.

In another aspect, the invention relates to compositions comprising a penetration enhancer (PE). The low penetration of drugs into the skin and the nail is the primary reason for the poor efficacy of topically applied drugs. The use of penetration enhancers is an effective strategy to improve the passive diffusion of the drug into the nail and the skin. Penetration enhancers (PEs) are chemical compounds which interact with the tissue and increase the diffusion of drug molecules through the biological membranes. The properties of an ideal penetration enhancer are (Williams, A. C. and Barry, B. W., 2004):

- Non-toxic, non-irritant, non-allergenic;
- Upon application, the enhancer should work promptly with a predictable and reproducible duration of activity;
- Pharmacologically inert;
- Should prevent loss of endogenous substances from the body;
- Should show reversible change in the barrier properties of the membrane; and
- Compatible with the active ingredient and other excipients in the formulation.

Penetration enhancers may act by one or more mechanisms such as disruption of the highly ordered structure of stratum corneum lipid, or interaction with intercellular protein, and as a result achieve improved partition of the drug, co-enhancer or solvent into the stratum corneum. In one embodiment, the permeability enhancer is selected from the group consisting of diethylene glycol monoethyl ether, or Transcutol®, N-methyl pyrrolidine, poly(oxyethylene) (4) lauryl ether, or BRIJ 30, polyoxyethylene (20) oleyl ether, or BRIJ 98, sorbitanlaurate, or SPAN 20, propylene glycol, polyethylene glycol 400, isopropyl myristate, thiourea, and urea-hydrogen peroxide. In another embodiment, the penetration enhancer is thiourea.

In one aspect, the invention relates to a composition comprising a hydrophobic plasticizer. The adhesives polymers used in the formulations of the invention are hydrophobic polymers, and drug release from hydrophobic polymers is typically slow. In one embodiment, addition of a hydrophobic plasticizer is useful in increasing polymer chain mobility. In one embodiment, the hydrophobic plasticizer is selected from the group consisting of triacetin (TAC) and triethyl citrate (TEC). In another embodiment, the hydrophobic plasticizer is triethyl citrate.

In one aspect, the invention relates to a composition comprising a pH adjuster. Because the antifungal used in the compositions of the invention, for example econazole nitrate, is a weak base, a reduction of pH can increase the drug solubility, by creating a higher concentration gradient which in turn promotes drug permeation into the tissues. In one embodiment, the pH adjuster is polyvinylpyrrolidone.

In one aspect, the invention relates to a composition comprising a solubilizer. In one embodiment, the solubilizer is propylene glycol.

In another aspect, the invention relates to a composition comprising pressure sensitive adhesive(s). The adhesive should ideally not cause any irritation to the skin or leave any residue upon removal. It should easily adhere to the site of application and maintain contact throughout the duration of application. The pressure sensitive adhesives (PSAs) used for transdermal patches are typically selected from the classes of polyisobutylenes, acrylates and polysiloxanes (Tan, H. and Pfister, W. 1999 and Williams, A. 2003). In one embodiment, the pressure sensitive adhesive(s) comprises an acrylate.

Formulations of the Invention

The present invention relates to the unexpected discovery that a formulation comprising an antifungal medication and a permeability enhancer can successfully treat skin or nail onychomycosis. In one embodiment, the antifungal medication is econazole nitrate, and in another embodiment, the permeability enhancer is thiourea. The key properties (Murdan, S. 2008) identified for a successful topical formulation for transungual delivery include ease of use, maintaining adequate contact with skin and/or nail, easy release and diffusion of drug from the formulation, high thermodynamic activity, ability to hydrate the nail, and presence of penetration enhancers.

In one embodiment, the concentration of econazole nitrate in the formulations of the invention is from 0.1% w/w to 25% w/w. In another embodiment, the concentration of econazole nitrate in the formulations of the invention is from 0.5% w/w to 15% w/w. In another embodiment, the concentration of econazole nitrate in the formulations of the invention is from 1% w/w to 10% w/w. In another embodiment, the concentration of econazole nitrate in the formulations of the invention is from 2.5% w/w to 5% w/w. In one embodiment, the concentration of econazole nitrate in the formulations of the invention is about 2.5% w/w.

In one embodiment, the concentration of thiourea in the formulations of the invention is from 0.1% w/w to 10% w/w. In another embodiment, the concentration of thiourea in the formulations of the invention is from 0.5% w/w to 5% w/w. In one embodiment, the concentration of thiourea in the formulations of the invention is about 1% w/w.

In one embodiment, the concentration of propylene glycol in the formulations of the invention is from 1% w/w to 25% w/w. In another embodiment, the concentration of propylene glycol in the formulations of the invention is from 2.5% w/w to 15% w/w. In another embodiment, the concentration of propylene glycol in the formulations of the invention is from 5% w/w to 10% w/w. In one embodiment, the concentration of propylene glycol in the formulations of the invention is about 10% w/w.

In one embodiment, the concentration of triethyl citrate in the formulations of the invention is from 1% w/w to 25% w/w. In another embodiment, the concentration of triethyl citrate in the formulations of the invention is from 2.5% w/w to 15% w/w. In another embodiment, the concentration of triethyl citrate in the formulations of the invention is from 5% w/w to 10% w/w. In one embodiment, the concentration of triethyl citrate in the formulations of the invention is about 10% w/w.

In one embodiment, the concentration of polyvinylpyrrolidone in the formulations of the invention is from 0.1% w/w to 5% w/w. In another embodiment, the concentration of polyvinylpyrrolidone in the formulations of the invention is from 0.5% w/w to 2.5% w/w. In another embodiment, the concentration of polyvinylpyrrolidone in the formulations of the invention is from 0.5% w/w to 1% w/w. In one embodiment, the concentration of polyvinylpyrrolidone in the formulations of the invention is about 1% w/w.

In one embodiment, the formulation of the invention is a paste. In another embodiment, the paste is tacky or adhesive. In one embodiment, one of the ingredients of the paste is an acrylate. In one embodiment, the concentration of acrylate in the formulations of the invention is from 50% w/w to 95% w/w. In another embodiment, the concentration of acrylate in the formulations of the invention is from 65% w/w to 85% w/w. In another embodiment, the concentration of acrylate in the formulations of the invention is from 70% w/w to 80% w/w. In another embodiment, the concentration of acrylate in the formulations of the invention is from 75% w/w to 80% w/w. In one embodiment, the concentration of acrylate in the formulations of the invention is about 75.5% w/w.

In one embodiment, the formulation of the invention is a solution. In another embodiment, the formulation of the invention is an emulsion. In another embodiment, the formulation of the invention is a cream. In another embodiment, the formulation of the invention can be formulated into liposomes and microdroplets. A formulation of the invention can be prepared as a mixture, as an admixture, in the same skin or nail topical formulation, in separate formulations, in extended release formulations, microcapsules, or any of the previously described embodiments.

As would be understood by one skilled in the art, an emulsion consists of a mixture of two or more immiscible liquids, i.e., contains multiple phases. Emulsions are distinct from solutions, which contain one or essentially only one phase. One of the liquids in an emulsion is the dispersed phase, and is dispersed in the other phase, which is the continuous phase. In one type of emulsion, a continuous liquid phase surrounds droplets of water, i.e., water-in-oil emulsion. In another type of emulsion, oil is dispersed within a continuous water phase, i.e., oil-in-water emulsion. As it would be understood by one skilled in the art, the phrases "water-in-oil" and "oil-in-water" are used for exemplification purposes only, as an emulsion can be generally formed by any two immiscible liquids, including two nonaqueous immiscible liquids. Emulsification is the process by which emulsions are prepared. In one embodiment, a formulation of the present invention is a component of an emulsion, such as a water-in-oil or an oil-in-water emulsion, including, but not limited to a lipid emulsion, such as a soybean oil emulsion. For example, a formulation comprising econazole nitrate dissolved in a solution comprising a nonaqueous solvent may also comprise a lipid emulsion or an oil-in-water emulsion.

In certain embodiments, the emulsion of the invention may have a lipid component. In various embodiments, the lipid component may comprise an amount ranging from about 1% to 99%, from about 5% to about 75%, from about 10% to about 60%, from about 20% to about 50%, or from about 30% to about 40%, v/v of the emulsion. In various embodiments, the lipid component of the emulsion may be soybean oil, long chain triglyceride, castor oil, corn oil, cottonseed oil, olive oil, peanut oil, peppermint oil, safflower oil, sesame oil, soybean oil, hydrogenated soybean oil, hydrogenated vegetable oil, medium chain triglycerides coconut oil, palm see oil and derivatives, medium chain (C8/C10) mono- and diglycerides, d-alpha-tocopherol, soy fatty acids, or combinations thereof.

In certain embodiments, the emulsion of the invention comprises econazole nitrate and a nonaqueous solvent, and may further comprise an emulsifier. An emulsifier is a substance that stabilizes an emulsion. An emulsifier may also be known as an emulgent. An emulsifier may also be a surfactant. In various embodiments, the emulsifier may be egg phospholipid, purified egg phospholipids, Polyoxyl 35 castor oil (Cremophor EL), Polyoxyl 40 hydrogenated castor oil (Cremophor RH 40), Polyoxyl 60 hydrogenated castor oil (Cremophor RH 60), Polysorbate 20, Polysorbate 80, d-alpha-tocopheryl polyethylene glycol 1000 succinate, Solutol HS-15, propylene glycol, or combinations thereof. Various concentrations of an emulsifier may be used with the present invention. For example, a formulation of the present invention comprising econazole nitrate may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an emulsifier.

In various embodiments, the econazole nitrate formulation(s) of the present invention may be a component of a liposome suspension. A liposome, for example, multilamellar, unilamellar, and/or multivesicular liposomes, is a microscopic, spherical, fluid-filled structure, with walls comprising one or more layers of phospholipids and molecules similar in physical and/or chemical properties to those that make up mammalian cell membranes. By way of nonlimiting examples, liposomes may be formed from a variety of natural membrane components, such as cholesterol, stearylamine, or phosphatidylcholine, such as for example described in U.S. Pat. Nos. 5,120,561 and 6,007,838, each of which is incorporated herein by reference in its entirety, or of pure surfactant components like DOPE (dioleoylphosphatidyl-ethanolamine). Liposomes may be formulated to incorporate a wide range of materials as a payload either in the aqueous or in the lipid compartments or in both. Generally, lipophilic active substances dissolve in the bilayer, amphiphilic substances become associated with the phospholipid membrane and hydrophilic substances occur in solution in the enclosed aqueous volume, such as for example described by Artmann et al., 1990, Drug Res. 40 (II) 12:1363-1365, incorporated herein by reference in its entirety.

Liposome formulations of the invention may comprise any range of liposome and econazole nitrate components, according to the methods and detailed description set forth herein. By way of a non-limiting example, a liposome component of a formulation of the invention may include from 0.1% to 99.9% liposome component, or more preferably, from 0.1%-50% liposome component, and even more preferably, from 0.1%-30% liposome component. In various embodiments, the liposome of the invention comprises cholesterol, stearylamine, phosphatidylcholine, dioleoylphosphatidylethanolamine, or combinations thereof.

In various embodiments, the econazole nitrate formulation of the present invention may also be a component of a micro-droplet. A micro-droplet of the invention consists of a sphere of organic liquid phase drug that ranges in diameter from about 200 Angstroms to about 10,000 Angstroms that is covered by a monolayer of a suitable lipid. Preferred lipids are phospholipids, which are natural constituents of biological membranes and as such are biologically compatible. Compounds useful for preparing microdroplets include phosphatidylcholine (lecithin), sphingomyelin, phosphatidic acid, phosphatidyl serine, phosphatidyl inositol, diphosphatidyl glycerol and phosphatidyl glycerol. Micro-droplets may be prepared by sonication, including probe or bath sonication, homogenization, microfluidization or by high intensity mechanical agitation. The preferred method of preparing the microdroplets of the invention is by sonication with a probe sonicator. Alternatively, micro-droplets may be prepared in a bath sonicator.

In various embodiments, the econazole nitrate formulations of the present invention may also be a component of a liquid suspension. Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropyl methylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

The formulation of the invention can also be administered as a slow release formulation, with a carrier formulation such as microspheres, microcapsules, liposomes, etc., as a topical ointment or solution, as known to one skilled in the art to treat or prevent skin or nail. By "slow release", "time-release", "sustained release" or "controlled release" is meant that the therapeutically active component is released from the formulation at a controlled rate such that therapeutically beneficial levels (but below toxic levels) of the component are maintained over an extended period of time ranging from e.g., about 12 to about 24 hours, thus, providing, for example, a 12 hour or a 24 hour dosage form. The combination product may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate, and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety, or lipids that may be formulated as microspheres or liposomes. Delayed or extended release properties may be provided through various formulations of the vehicle (coated or uncoated microsphere, coated or uncoated capsule, lipid or polymer components, unilamellar or multilamellar structure, and combinations of the above, etc.).

In various embodiments, the econazole nitrate formulations of the present invention may also impregnate or coat a material, which can further be used topically. Methods for impregnating or coating a material with a chemical formulation are known in the art, and include, but are not limited to methods of depositing or binding a chemical formulation onto a surface, methods of incorporating a chemical formulation into the structure of a material during the synthesis of the material, e.g., such as with a physiologically degradable material, and methods of absorbing an aqueous or oily solution or suspension into an absorbent material, with or without subsequent drying. Methods for impregnating or coating a material with a formulation of the invention are known in the art, and include also, but are not limited to, methods of depositing or binding a tacky or glue paste formulation onto a surface, for example a tacky or glue paste comprising an acrylate.

In one embodiment, the methods for impregnating or coating a material with a formulation of the invention are used to fabricate a patch, including for example a skin or a nail patch. In one embodiment, the formulation of the invention used in the fabrication of the patch comprises a polymer. For effective drug delivery into and across the nail, it is important to obtain a favorable balance between the solubility of the drug dose in the polymer, release of the drug from the dosage form and the partitioning of the drug from the dosage form to the membrane. The selection criteria for the polymer matrix of a patch include the patch design, stability of the drug (no crystallization), compatibility with penetration enhancers, duration of wear (24 hrs), ease of manufacture, and ease of use. In one embodiment, the patch of the invention establishes a high drug release rate. In another embodiment, the patch adheres to the nail for 24 hours, which requires adequate tack adhesion. In another embodiment, the drug remains in a solubilized form in the patch without any crystallization for the consideration of uniformity and stability. In one embodiment, the patch comprises a backing membrane (BM). In another embodiment, the patch comprises an adhesive. In another embodiment, the patch comprises a plasticizer. In another embodiment, the patch comprises a release liner (RL). In one embodiment, the backing membrane is inert and compatible with the other components of the patch (Gungor, S. et al 2012 and Williams, A., 2003). In another embodiment, the backing membrane is impermeable to the drug and penetration enhancers if they are present in the formulation. In case of transungual patches, occlusive backing membrane was proposed to maintain the optimal hydration of the nail plate and thereby increase transungual permeation of the antifungal drugs. The release liner should be impermeable to the components of the matrix, occlusive and easily removed from the adhesive layer prior to application of the patch on the skin (Güngör, S. et al 2012 and Williams, A., 2003).

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. For example, a unit dose may be such that an econazole nitrate composition is coating a backing material to forma patch. The unit dose may further comprise a release liner which can be removed to expose the econazole nitrate composition which can then be applied to skin or nail. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. Pharmaceutical compositions that are useful in the methods of the invention may be prepared, packaged, or sold in formulations suitable for topical, or another route of administration.

Although the description of pharmaceutical compositions provided herein are principally directed to pharmaceutical compositions which are suitable for ethical administration to humans, it will be understood by the skilled artisan that such compositions are generally suitable for administration to animals of all sorts, including mammals. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention comprise an effective amount of an antifungal medication dissolved or dispersed in a pharmaceutically acceptable carrier. In one embodiment, the antifungal medication is econazole nitrate. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least econazole nitrate, and additional active and non-active ingredients will be known to those of skill in the art in light of the present disclosure, as exemplified by "Remington: The Science and Practice of Pharmacy," 20th Edition (2000), which is incorporated herein by reference in its entirety. For animal (for example, human) administration, it will be understood that preparations should meet sterility, pyrogenicity, general safety and purity standards as required by FDA Office of Biological Standards.

In various embodiments, the compositions of the present invention further comprise cyclodextrin. Cyclodextrins are a general class of molecules composed of glucose units connected to form a series of oligosaccharide rings (See Challa et al., 2005, AAPS PharmSciTech 6:E329-E357). Cyclodextrins have been employed in formulations to facilitate the delivery of various drugs, for example cisapride, chloramphenicol, dexamethasone, dextromethoraphan, diphenhydramine, hydrocortisone, itraconazole, and nitroglycerin (Welliver and McDonough, 2007, Sci World J, 7:364-371). In various embodiments, the cyclodextrin of the invention is hydroxypropyl-Beta-cyclodextrin, sulfobutylether-beta-cyclodextrin, alpha-dextrin or combinations thereof. In certain embodiments, cyclodextrin may be used as a solubilizing agent.

In various other embodiments, compositions of the present invention may comprise human serum albumin purified from plasma, or recombinant human serum albumin. In certain embodiments, human serum albumin may be used as a solubilizing agent. In other embodiments, the compositions of the invention comprise propylene glycol.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents which may be included suitable for use include sterile aqueous solutions or dispersions and sterile powders for the extemporaneous preparation of sterile solutions or dispersions (U.S. Pat. No. 5,466,468, specifically incorporated herein by reference in its entirety). Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired. A particle filter or microbe filter may be used and may be necessary according to the route of administration desired.

In addition to the active ingredient, a pharmaceutical composition of the invention may further comprise one or more additional pharmaceutically active agents. One non-limiting example of such an additional pharmaceutically active agent is an antimicrobial agent, such as an antibiotic. In one embodiment, the antibiotic is gentamicin.

Controlled- or sustained-release formulations of a pharmaceutical composition of the invention may be made using conventional technology.

The pharmaceutical compositions may be prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other formulations which are useful include those which comprise the active ingredient in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The solution and/or composition may also be sterilized prior to administration. Methods for sterilization are well known in the art and include heating, boiling, pressurizing, filtering, exposure to a sanitizing chemical (for example, chlorination followed by dechlorination or removal of chlorine from solution), aeration, autoclaving, and the like.

Kits

The invention also relates to a kit for treating a skin or nail disorder in a subject. In one embodiment, the kit includes a patch comprising an econazole composition, and an instruction manual. The patch may be sterile. In one aspect, a patch that offers many advantages, such as, for example, ease of application, unit dose configuration, and excellent nail occlusion, is contemplated.

The pharmaceutical compositions of the invention may be provided to the subject or the medical professional in charge of dispensing the composition to the subject, along with an instructional material. In one embodiment, the instructional material is part of a kit. The instructional material includes a publication, a recording, a diagram, or any other medium of expression, which may be used to communicate the usefulness of the composition and/or compounds used in the practice of the invention in a kit. The instructional material of the kit may, for example, be affixed to a container that contains the composition used in the practice of the invention or shipped together with a container that contains the composition. Alternatively, the instructional material may be shipped separately from the container with the intention that the recipient uses the instructional material and the composition cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Methods of Treatment, Delivery and Dosing

The invention also relates to a method of treating a disorder in a subject. In one embodiment, the subject is human. In another embodiment, the disorder is a skin or nail disorder. Human nail is composed of the nail plate, nail folds, nail matrix, nail bed, and the hyponychium. The nail matrix forms the nail plate whose growth rate varies considerably among individuals. An average value of 3 mm per month (fingernails) and 1 mm per month (toenails) is often used. Thus, on average, a normal fingernail grows out completely in about 6 months while a normal toenail in about 12-18 months. The most obvious part of the nail unit, the nail plate, is a thin (0.25-0.6 mm), hard, yet slightly elastic, translucent, convex structure. It is composed of approximately 80-90 layers of dead, keratinized, flattened cells which are tightly bound together. The cells at the dorsal surface of the plate overlap, producing a smooth and poorly permeable surface. A cross-section view highlights the plate's compact nature. The nail plate can be divided into two layers: dorsal and ventral, based on differential ultrasound transmission. The ventral layer is more plastic, while the dorsal one is hard and brittle. Some authors consider the nail plate to consist of three strata: dorsal, intermediate and ventral, the latter being taken as the few layers of cells, which connect the nail plate to the nail bed. Chemically, the nail plate consists mainly of proteins, namely low sulphur keratins, and high sulphur and high glycine/tyrosine proteins. The latter two groups are believed to form an interfilamentous matrix, while the low sulphur keratins form 10 nm filaments. The plate also contains water at 10-30%, and very small amounts of lipid at 0.1-1%.

In another embodiment, the disorder is a skin disorder. Human skin can be considered to have three distinct layers of tissue (Trop J Pharm Res, April 2009): 1) non-viable epidermis (stratum corneum), 2) viable dermis, and 3) subcutaneous connective tissue (hypodermis). Stratum corneum is the outer most layer of skin. This is the actual physical barrier to most substances that come in contact with the skin. The stratum corneum is 10 to 20 cell layers thick over most of the body. It consists of lipid (5-15%) including phospholipids, glycosphingolipid, cholesterol sulfate and neutral lipid. The protein (75-85%) is mainly keratin. Beneath the epidermis is the dermis. It is a structural fibrin which has a thickness range from 2000 to 3000 µm and consists of a matrix of loose connective tissue composed of fibrous protein embedded in an amorphous ground substance. The subcutaneous tissue is not actually considered a true part of the structured connective tissue is composed of loose textured, white, fibrous connective tissue containing blood and lymph vessels, secretory pores of the sweat gland and cutaneous nerves. Most investigators believe the drug permeates through the skin and enters the circulatory system before reaching the hypodermis. Although the fatty tissue could serve as a depot of the drug. Permeation of skin can occur by diffusion via (Thong, H. Y. et al 2007): 1) transdermal permeation, through the stratum corneum, 2) intercellular permeation, through the stratum corneum, and 3) transappendaged permeation, via the hair follicle, sebaceous and sweat glands.

In another embodiment, the disorder is onychomycosis. Onychomycosis traditionally referred to a non-dermatophytic infection of the nail but is now used as a general term to denote any fungal nail infection (tinea unguium specifically describes a dermatophytic infection of the nail plate). It is caused by dermatophytes, yeasts and molds. The fungi that cause onychomycosis are the dermatophytes, yeasts and molds. Studies of sampled material from infected nails have identified that over 90% of onychomycoses are caused by two dermatophytes: *Trichophyton rubrum* (71% of all infections) and *Trichophyton mentagrophytes* (20%) (FIG. 1.1). The pathological distribution of the different pathogens varies. Rather, it depends on various factors such as geography, climate and migration. Among the yeasts, the most commonly implicated organism in onychomycosis is *Candida albicans*. Although yeast infections most commonly affect the fingernails, *C. albicans* infections may also account for approximately 10% of cases of toenail onychomycosis. Saprophytic molds, particularly *Scopulariopsis brevicaulis*, can be isolated from approximately 11% of cases of toenail onychomycosis.

There are five major classic types of onychomycosis, most of which can be further subdivided. Distal subungual onychomycosis can be further subdivided into distal lateral subungual onychomycosis and endonyxsubungual onychomycosis. Distal lateral subungual infection, the most common form of the disease, begins on the distal section of the nail and spreads under the nail, infecting the nail bed. White superficial onychomycosis (WSO) is more commonly associated with *T. mentagrophytes* var. *interdigitale* than with *T. rubrum* infections. However, it is relatively simple to obtain a sample of the fungi responsible for infection. Superficial onychomycosis infections are relatively simple to treat and respond well to topical therapy. Proximal subungual onychomycosis relates to fungal penetration of the newly formed nail plate through the proximal nail fold. It is the least common form of tinea unguium in healthy people, but is found more commonly when the patient is immunecompromised. Candidal onychomycosis relates to *Candida* species invasion of the fingernails, usually occurring in persons who frequently immerse their hands in water. This normally requires the prior damage of the nail by infection or trauma. Total dystrophic onychomycosis is used to describe end-stage nail disease, although some clinicians consider it a distinct subtype. It may be the end result of any of the four main patterns of onychomycosis. The entire nail unit becomes thick and dystrophic.

Onychomycosis impairs normal nail functions such as appendage skin protection, added grip, strengthening the tip of appendages. This causes considerable pain, interferes with daily activities, and has negative psychosocial effects. According to a study conducted by a total of 258 patients with confirmed onychomycosis were surveyed by telephone at three centers. Responses to a standardized quality-of-life questionnaire were analyzed for patient demographics, physical and functional impact, psychosocial impact, and economic impact. Highest positive responses were nail-trimming problems (76%), embarrassment (74%), pain (48%), nail pressure (40%), and discomfort wearing shoes (38%). Ability to pick up small objects was impaired in 41% of subjects with fingernail involvement. More than 58 onychomycosis-related sick days and 468 medical visits (1.8 per subject) were reported during a 6-month period (J Am Acad Dermatol 1998). Furthermore, patients who have onychomycosis may develop psychological disorders related to concern about the abnormal appearance of their nails. Fungal nail infections may also lead to the spread of organisms to adjacent and distant areas of the skin. This leads to further impairment of the quality of life, with mental and social implications leading to reduced self-esteem and limitation of interaction with others. The clinical presentation of dystrophic nails should alert the clinician to the possibility of onychomycosis; however, because fungi cause only about half of all nail dystrophies, the use of appropriate diagnostic techniques including direct microscopy and fungal culture is important to ensure correct diagnosis and treatment. The clinical appearance of the nail and the patient's history will help differentiate fungal from non-fungal etiologies of nail dystrophies (BONI E. et al, 1998).

The methods of the present invention can comprise administering an econazole nitrate formulation of the invention alone, or in combination with other agents that modulate a particular pathological process. For example, agents comprising an econazole nitrate formulation of the invention can be administered in combination with one or more different anti-fungal, and/or one or more anti-inflammatory agents. As used herein, two agents are said to be administered in combination when the two agents are administered simultaneously or are administered independently in a fashion such that the agents will act at the same time.

The disorders treatable by means of the present invention occur in mammals. Mammals include, for example, humans, as well as pet animals such as dogs and cats, laboratory animals such as rats and mice, and farm animals such as horses and cows.

The amount of econazole nitrate composition to be administered depends on the particular indication desired. For example, the dose will depend on the type of skin or nail disorder intended to be treated, in particular the type of onychomycosis to be treated. The dose may be different, for instance, if the delivery of the econazole nitrate is intended to reduce a skin, as opposed to a nail condition. The dose may be different also if the delivery of the econazole composition is intended to treat distal subungual onychomycosis, distal lateral subungual onychomycosis, endonyx-subungual onychomycosis, white superficial onychomycosis, superficial onychomycosis infections, proximal subungual onychomycosis, candidal onychomycosis, or total dystrophic onychomycosis. The subject's physical characteristics may also be important in determining the appropriate dosage. Characteristics such as weight, age, and the like may be important factors. For example, depending on the skin or nail disorder intended to be treated, the econazole nitrate composition may have increased or decreased potency with age. The particular dosage may also be dependent on the dosing regimen chosen, such as for example, the econazole composition may be delivered continuously or periodically.

Econazole nitrate compositions of the present invention may be delivered topically. Topical drug delivery is especially suitable for onychomycosis (2-13%) and nail psoriasis (1-3%), which affect general population, and make up the bulk of nail disorders. Topical therapy avoids the adverse events and drug interactions of the systemic antifungal agents. It is non-invasive when compared to the injection anti-psoriatic agents into the nail folds. The target sites for the treatment of onychomycosis and other nail disorders resides in the nail plate, nail bed and nail matrix. Various topical therapies for nail disorders, which have been studied so far, are: lacquers, gels/solutions, creams/pastes, colloidal systems/liposomes, powders, aerosols/foams/sprays. In one aspect, the invention concerns the development of a nail bandage. In one embodiment, the bandage consists of a T-shaped, or other appropriately shaped adhesive backing, and a flexible pad having backing with a nail-shaped cavity (containing active solute along with other sedatives) (T Praveen Kumar et. al, IJPRR 2013).

Other routes of administration to the affected area which are contemplated include injection, infusion, continuous infusion, localized perfusion bathing target cells directly, via a catheter, via nanoparticle delivery, intravenous, intramuscular, cutaneous, subcutaneous, transdermal, or topical administration. In certain embodiments, topical administration includes administration in a carrier vehicle, a topical control release patch, in a wound dressing, a hydrocolloid, a foam, a hydrogel, a cream, a gel, a lotion, an ointment, a liquid crystal emulsion, and/or a micro-emulsion. An appropriate biological carrier or pharmaceutically acceptable excipient may be used. Compounds administered may, in various embodiments, be racemic, isomerically purified, or isomerically pure.

Topical Formulations.

Topical formulations may be in any form suitable for application to the body surface, and may comprise, for example, a solution an ointment, cream, gel, lotion, paste or the like, and/or may be prepared so as to contain liposomes, micelles, and/or microspheres. In one embodiment, the compositions of the invention are liquid solutions topical formulations. In one embodiment, the solution is dropped onto the surface of skin or nail, while in other embodiments the solution is sprayed onto the surface of the skin or nail. In certain embodiments, topical formulations herein are ointments, creams and gels. In one embodiment, the topical formulation is part of a medical patch.

Transdermal and Transungular Administration.

Topical administration may also involve the use of transdermal and transungular administration, such as transdermal patches or iontophoresis devices, or transungular patches or iontophoresis devices. Transdermal compound administration, which is known to one skilled in the art, involves the delivery of pharmaceutical compounds via percutaneous passage of the compound into the systemic circulation of the patient. Other components may be incorporated into the transdermal patches as well. For example, compositions and/or transdermal patches may be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions may include creams, sprays, lotions, gels, ointments, eye drops, nose drops, ear drops, and the like. In such dosage forms, the compositions of the invention may be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions may contain polyethylene glycol 400. They may be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, may be impregnated with the compositions in solution, lotion, cream, ointment or other such form may also be used for topical application.

The compositions may also be applied topically using a transdermal or transungular system, such as one of an acrylic-based polymer adhesive with a resinous crosslinking agent impregnated with the composition and laminated to an impermeable backing. Examples of suitable skin or nail contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.

Additional Administration Forms.

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Pat. App. Nos. 20030147952, 20030104062, 20030104053, 20030044466, 20030039688, and 20020051820. Additional dosage forms of this invention also include dosage forms as described in PCT App. Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

In one embodiment, the method comprises the step of administering a composition of the invention in a biocompatible, biodegradable matrix, for example in the form of a gel or polymer which is preferably suited for topical administration to skin or nails.

It is contemplated that any embodiment discussed in this specification may be implemented with respect to any method or composition of the invention, and vice versa. Furthermore, compositions of the invention may be used to achieve methods of the invention.

Other objects, features and advantages of the present invention will become apparent from the detailed description herein. It should be understood, however, that the detailed description and the specific examples, while indicating specific embodiments of the invention, are given by way of illustration only, since various changes and modifications within the spirit and scope of the invention will become apparent to those skilled in the art from this detailed description.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials

Econazole nitrate (Spectrum Chemical MFG), PG (MP Biochemicals), TU (Acros Organics), gentamicin sulfate (Sigma Aldrich), Bovine serum albumin (lyophilized powder; SIGMA), Franz diffusion cells and neoprene nail adapters (PermeGear), Triethyl citrate and triacetin (Acros organics), Kollidon 30 polyvinylpyrrolidone (BASF), Acrylates polymer (DURO-TAK® 87-9301, DURO-TAK® 87-4287, DURO-TAK® 87-4098, DURO-TAK® 87-2287; Henkel, N.J.), Polyisobutylene (DURO-TAK® 87-6908), Silicone PSAs compatible with amine functional drugs (Dow Corning® BIO-PSA 7-4302, BIO-PSA 7-4502, and BIO-PSA 7-4602), Non-occlusive ethylene vinyl acetate (EVA) backing membrane 9707 (3M™ CoTran™), fluoropolymer coated polyester film 9742 (3M™ Scotchpak™), Human cadaver skin and toe nails (Anatomy Gifts Registry, Hanover, Md.).

Example 1: Nail Patch Design and Construction

The design for the transungual patch was based on the simple DIA design as shown in FIG. 1. The drug (EN) and the PEs, thiourea (TU) and propylene glycol (PG), were dissolved or uniformly dispersed in the pressure sensitive adhesive(s) (PSAs), and spread onto a release liner. The drug (EN) and the nail PE (TU) were weighed out in a glass bottle and dissolved in solvent (methanol) and vortexed for 1 min. Then PG was weighed and added as solubilizer for EN and plasticizer for the patch. The solution was vortexed with the methanol as solvent until a single phase was obtained. Afterwards, the hydrophobic plasticizers triethyl citrate and hydrophilic polymer polyvinylpyrrolidone were weighed and mixed with the solvents prior to addition of PG. Finally the polymer was weighed out into the glass bottle and vortexed for 5 min to form a homogenous mixture. The formulae for the patch include but are not limited to those in Table 3. The bottles were then placed on the bottle roller and mixed overnight at medium speed to complete the mixing and remove the air bubbles generated during vortexing the polymer. The mixture was then poured on to the release liner and spread into a layer with uniform thickness. The film was air dried in the hood for 24 hrs then oven dried at 50° C. for 3 hr. The backing membrane was laid onto the dry film.

Example 2: Formulae for the Nail Patch

TABLE 3

| Formulae | Econazole nitrate | Thiourea | Propylene glycol | Triethyl citrate | Poly-vinylpyrrolidone | Duro-tak 4098(acrylate) |
|---|---|---|---|---|---|---|
| Percentage | 2.5% | 1% | 10% | 10% | 1% | 75.5% |
| Function | Antifungal drug | Penetration enhancer | solubilizer | plasticizer | pH adjuster | Pressure sensitive adhesive |

Determination of Concentration of TU

Films with 1% TU did not show any crystallization. However, the crystallization increased in films with 2.5% TU and 5%, TU respectively. Since there was a concentration dependent increase (visual observation) in the number of crystals throughout the film and no crystallization in the film with 1% TU, it was concluded that it is TU that crystallizes out of the acrylate matrix at 2.5% and 5% load. A slight crystallization of econazole nitrate has been observed in acrylate PSA patch at a drug load of 5% w/w with no PG added. Crystal formation was also found to significantly reduce the tack of the film. Even with the addition of 20% PG, TU crystallized upon drying. Therefore, it was concluded that all the future screening studies will be carried out at 1% TU.

Screening of Acrylates

The percentage of TU was maintained at a concentration off 1%. Three concentrations of EN (1% w/w, 2.5% w/w and 5% w/w) and three concentrations of PG (5% w/w, 10% w/w and 20% w/w) were evaluated. The acrylate films were first fabricated with DURO-TAK® 87-4098. The total weight of the mixture was 5 g. Methanol was the only solvent used for dissolving the components in the acrylates films. The purpose of this was to screen out what concentration of EN and PG could be added into the polymer to form an acceptable patch. Then according to the EN and PG concentration determined from the DURO-TAK® 87-4098 films, fabricated patches using acrylate grades DURO-TAK® 87-2287, DURO-TAK® 87-4287 and DURO-TAK® 87-9301.

It was noted that compared to increasing the concentration of EN, increasing the PG level was more effective at increasing the drug release rate. It was also noted that the tack for each of the acrylates dropped considerably when the PG content was increased. Hence the PG concentration was kept at 10% w/w for the acrylate patch screenings. This provides an enhanced drug release percentage but also maintains satisfactory tack of the adhesive. When raised the EN concentration to 5% w/w, crystallization occurred. Even though 2.5% w/w EN did not provides the most drug release, it has higher drug release rate compare to the 1% w/w EN.

Addition of Hydrophobic Plasticizers

Drug release from hydrophobic polymers is slow. The adhesives polymer used are hydrophobic polymers. To increase polymer chain mobility, the addition of a hydrophobic plasticizer was considered. Triacetin (TAC) and triethyl citrate (TEC) were the selected plasticizers. The adhesive polymer acrylate had been selected as the best polymer system. TAC or TEC was added into the acrylate polymer at three different levels. These were, 5%, 10% and 20% (based on the 5 g matrix weight).

20% of plasticizer caused crystallization in all polymers. So a plasticizer percentage at 10% will provide a higher drug release rate without crystallization. It was determined that polymers 4098, 4287, 2287 all have drug release rate above 20 μg/cm²/hour DURO-TAK 4287 and 2287 provided for the highest drug release. Upon storage, DURO-TAK 4287 and 2287 contained crystals inside the matrix. Both DURO-TAK 4287 and 2287 polymer have the functional group —OH. It is hypothesized that this functional group may be incompatible with EN. This induces crystallization with time. This can be also observed from the interaction plot. With DURO-TAK 4098 and 9301, increasing the plasticizer percentage increased the drug release rate. In DURO-TAK 4287 and 2287 increasing the plasticizer decreased the drug release rate. This is an indication of crystallization.

TEC was shown to be the preferred plasticizer at 10% concentration. Polymer 4287 and 2287 have the preferred drug release properties but these polymers may not be compatible with EN. This causes a physical stability problem DURO-TAK 4098 provides for the appropriate amount of EN drug release without the physical stability issues of other polymers.

Addition of Polyvinylpyrrolidone

Because econazole nitrate is a weak base, a reduction of pH can increase the drug solubility. This would create a higher concentration gradient to promote drug permeation into the tissues. Polyvinylpyrrolidone, is a water-soluble polymer made from the monomer N-vinylpyrrolidone. It has many uses and was proposed in these formulations to avoid crystallization. Kollidon 30 in solution has a pH range of 3-5. Therefore, by adding 1-5% of polyvinylpyrrolidone it can reduce the pH of the adhesive. The pH of 1% and 5% (based on 5 g matrix weight) of polyvinylpyrrolidone in water solution were tested using a pH meter. The drug saturation solubility test and also the nail penetration study test in 1% and 5% PVP solution were also conducted. The 1% and 5% of polyvinylpyrrolidone were added into the acrylate patch. It was hypothesized that PVP would increase the drug release and permeation of EN.

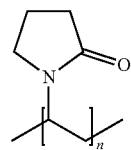

Polyvinylpyrrolidone

After dissolving 1% and 5% of PVP in water to get a solution, the pH was checked and recorded. The 1% PVP solution has a pH of 4.5 and the 5% PVP solution has a pH of 3.5. In the drug saturation solubility study, PVP 1% and 5% solution both have significantly higher EN solubility compare to phosphoric buffer at pH 7.4 and pH 5 (P<0.05). There is not a significant difference in the saturation solubility of EN in 1% PVP and 5% PVP. In the nail penetration study, the EN amount penetrated into the nail plate, for 1% and 5% PVP group, are significantly higher compared to the phosphoric buffer pH 7.4 and pH 5 groups. Both the solubility study and the permeation study indicate that 1% and 5% PVP groups increases EN saturation solubility. This results in an increased and EN penetration into the nail plate. PVP enhances the solubility of EN much greater than would be expected by just decreasing the pH. This means that PVP is a solubility enhancer for EN.

The surface pH of different patches were checked by using pH strips on hydrated patch surface. It was determined that with 1% PVP it can bring the patch pH down to the 5-6 range, and with 5% PVP, the pH of the patch can be even lower (pH 4-5). The drug release rate in absence of the PVP is 22.347 μg/cm²/hour, and with addition of 1% and 5% of PVP, it increased to 26.713 μg/cm²/hour and 27.853 μg/cm²/hour accordingly. This indicates that with lower pH, there is more ionized form of EN in the patch, therefore, the release rate increased.

Example 3: In-Vitro Skin Permeation of Econazole Nitrate

Figure 2:
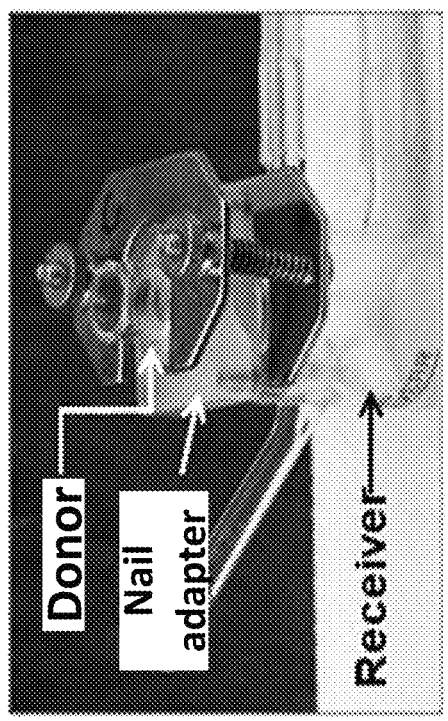
FIG. 2 is a series of pictures depicting, respectively.
Figure 2:
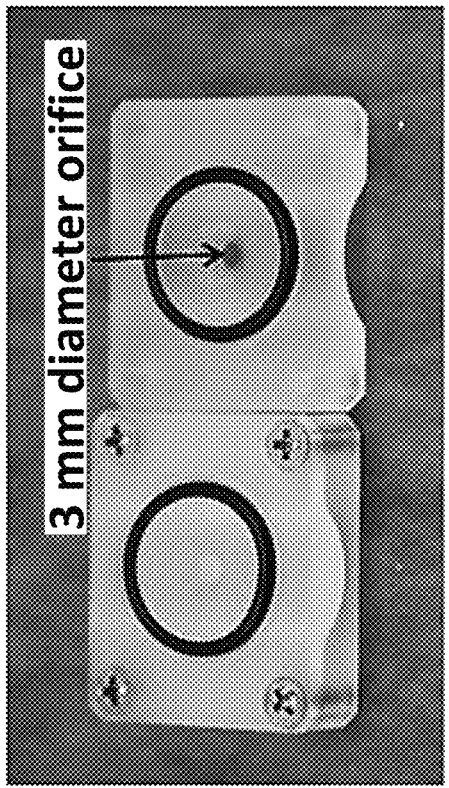

The patch was studied for the transdermal permeation of EN using human cadaver skin and Franz diffusion cells (FIG. 2A). Three films each with an area of 4 cm² square patch were cut from patch film. The skin was cut into 1.5 cm by 1.5 cm pieces, and mount on the Franz diffusion cells with orifice diameter of 9 mm (FIG. 2B). The release liner was removed from the films and the matrix surface was placed in contact with the skin. The area of 0.64 cm² of the skin was in contact with the receiving medium. The receiver compartment was sampled at 1, 2, 4, 8, 12 and 24 hr by withdrawing 0.5 mL of the receiving medium and replacing with equal volume of pH 7.4 PBS. At the end of 24 hr, epidermis and dermis were heat separated and extracted for EN content.

Example 4: In Vitro Transungual Permeation of Econazole Nitrate

The cadaver toenails were cut into 7 mm×7 mm (49 mm$^2$) pieces. The nail pieces were then hydrated at 100% RH overnight prior to start of experiment. The hydrated nail pieces were placed in the neoprene nail adapters (FIG. 2A) with orifice diameter of 5 mm. The receiver compartment was filled with pH 7.4 PBS (3 mL) containing 0.1% w/v gentamicin sulfate and the assembly was maintained at 32±1° C. throughout the duration of the experiment. Each sample was tested in triplicate. The patch in absence of thiourea was used as the control. The patches with diameter of 5 mm were cut. The release liner was removed and the drug matrix was placed in contact with the nail. The new patch was applied every 24 hrs for 14 days. Throughout the duration of the study, the Franz cells were dosed with a new patch daily. On the days 2, 4, 6, 8, 10, 12 and 14, 0.5 mL of the sample was withdrawn from the receiver compartment and replaced with equal volume of new receiving medium.

Example 5: In-Vitro Skin Permeation Study

After 24 hours study, there is no drug amount appeared in the receiver compartment. This can be explained by the Log P (5.5) of econazole nitrate, the drug would prefer to stay in the Stratum Corneum, which is a hydrophobic instead of diffusing into the buffer. This will be beneficial because the main goal of topical delivery is to maximize skin exposure and minimize the systemic exposure of the drug. This reduces the chances of adverse side effects and drug-drug interactions.

Figure 3:
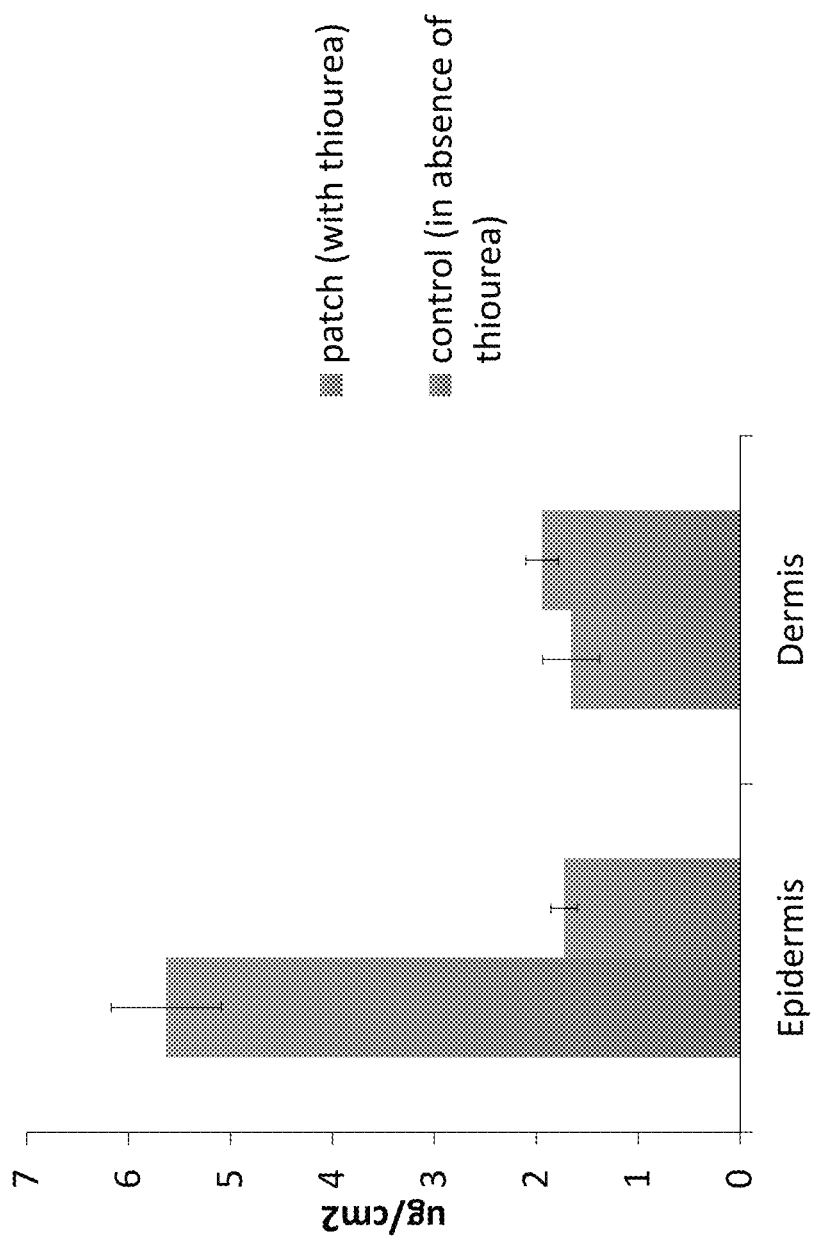
FIG. 3 is a comparative graph depicting the accumulation of econazole nitrate within epidermis and dermis with thiourea and in absence of thiourea.

There's significantly improvement on the drug amount in the epidermis upon the use the thiourea. The drug amount increase from 1.73 ug/cm$^2$ to 5.63 ug/cm$^2$ (FIG. 3), while for the drug amount in the dermis, there's no significant difference between the two. So actually penetration enhancer thiourea can push more drug into the epidermis but not dermis, which is a benefit for the certain disease onychomycosis.

Example 6: In-Vitro Transungual Permeation Study

The ability of thiourea in enhancing drug penetration was confirmed in the in vitro transungual permeation of EN through human cadaver toenail.

Figure 4:
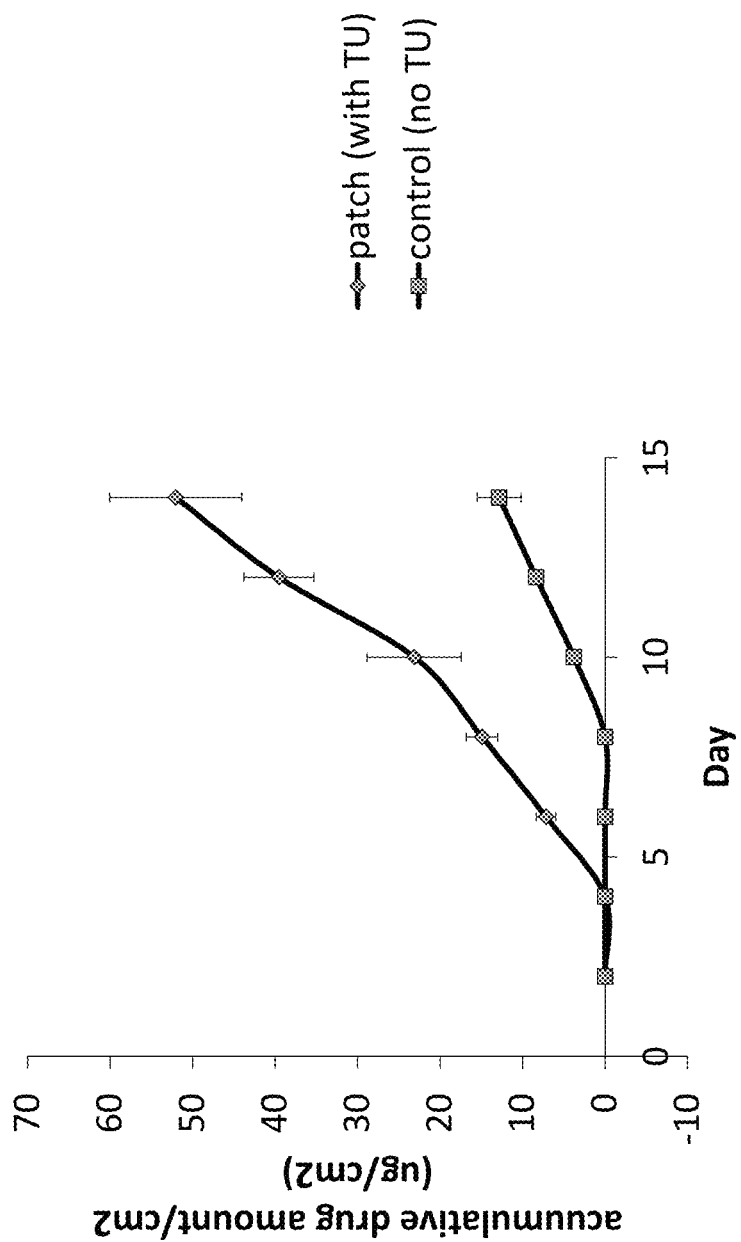
FIG. 4 is a comparative graph depicting transungual permeation of econazole nitrate with thiourea and without thiourea.
Figure 5:
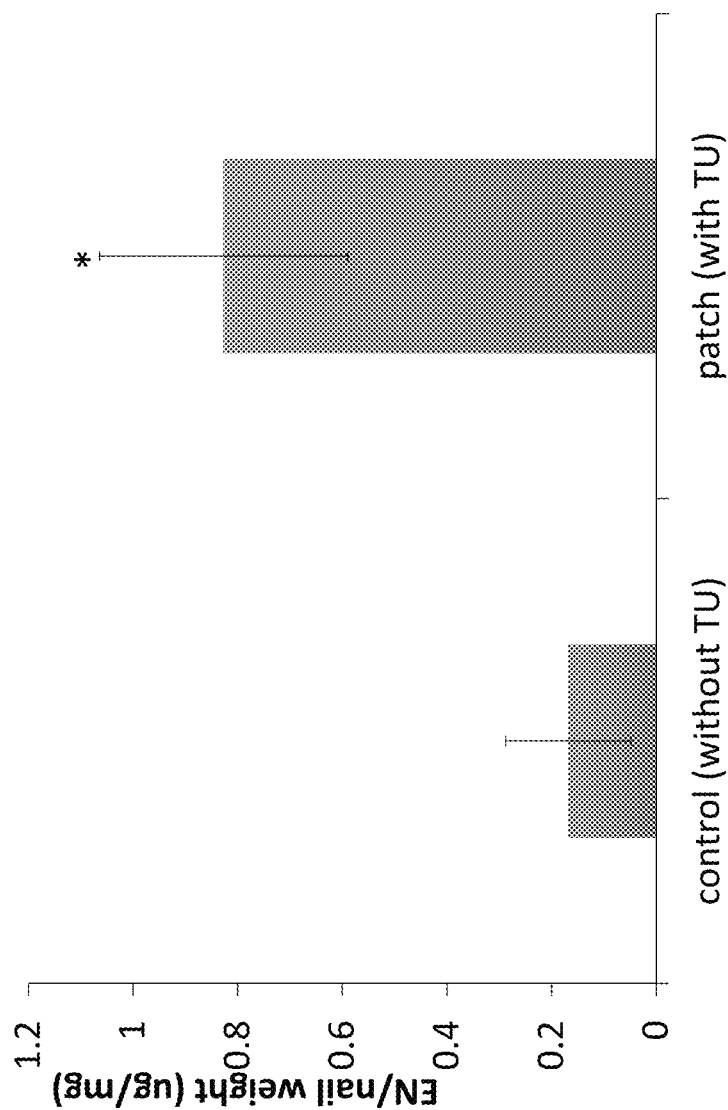
FIG. 5 is a comparative graph depicting the amount of econazole nitrate inside of the nail plate with thiourea and without thiourea.

In FIG. 4, upon the use thiourea, the drug accumulation in the receiver side is significantly higher compare to the one without. The lag time decreased from 8 days to 6 days, and the flux increased from 2 ug/cm$^2$/day to 4.33 ug/cm$^2$/day. In FIG. 5, there's significantly increase drug amount in nail plate upon the presence of thiourea, it's acting directly on the nail plate and break the disulphide bond inside of it, lead to more spots open for the drug to bind.

Example 7: Econazole Vs. Ciclopirox Lag-Time Comparison

Materials and Methods

Patch formulations were made using a film drying technique. Generally, the drug and permeation enhancers were dissolved in solvent containing polymer solutions. These solutions were cast onto a PTFE liner and then dried. A polyvinyl acetate release liner was added to the back.

Nail Permeation

Human Cadaver Nails were acquired from Anatomy Gifts Registry and cut to a 5 mm by 5 mm size. The nail pieces were mounted in a Nail adapter and mounted on a Franz Cell. The receiver media was pH 7.4 Phosphate buffered saline. For EN patches 4% Bovine Serum Albumin was added to improve sink conditions. For each formulation, a patch was applied daily and the receiver compartment of the Franz cell was sampled for assay. For ciclopirox formulations the permeation studies were conducted for 28 days. For Econazole formulations the permeation studies were 14 days long. The formulations of each patch are summarized in Table 4. CPO patches required the use of a hydrophilic polymer (HPMC). An appropriate rubber based adhesive would be needed to adhere the patch to the nail. EN formulations used an ethylhexyl acrylate based pressure sensitive adhesive. No additional adhesive would be needed for these formulations.

TABLE 4

Antifungal formulations

| Drug | Prototype | Formulation |
|---|---|---|
| EN | H4 | 2.5% EN, 1% TU, 10% PG, 10% TEC, 1% PVP, 75.5% 4098 (acrylate polymer) |
| EN | P1 | 2.5% EN, 1% TU, 10% PG, 10% TEC, 1% PVP, 75.5% 4098 (acrylate polymer) |
| EN | Control | 2.5% EN, 10% PG, 10% TEC, 76.5% 4098 (acrylate polymer) |
| CPO | Patch | 10% CPO, 10% TU, 15% PG in HPMC |
| CPO | PenLac | Nail Lacquer |

Table 5 contains the permeation data for the EN and CPO prototypes. Nail is a hydrophilic matrix; therefore, it was expected that the CPO would have greater permeation. In our experiments EN had much better permeation and a reduced lag-time.

TABLE 5

Permeation Summary

| Patch | Lag time (day) | Permeation flux (µg/cm2/day) | $C_{14days}$ (µg/mL) |
|---|---|---|---|
| Control | 8.1 ± 1.16 | 2.57 ± 0.53 | 2.52 ± 0.52 |
| H4 | 5.87 ± 0.51 | 5.78 ± 0.89 | 10.22 ± 1.57 |
| P1 | 5.69 ± 0.59 | 5.92 ± 0.94 | 11.07 ± 1.63 |
| CPO Prototype Patch | 11.45 ± 1.25 | 4.1 ± 0.59 | 4.08 ± 0.67* |
| Penlac ® | 18.36 ± 1.20 | 0.98 ± 0.56 | 0.79 ± 0.46* |

*Concentration after 32 days

It was hypothesized that this is due to the reduced keratin binding of econazole compared to CPO. The keratin binding of Keratin is 96%. Using thiourea as a permeation enhancer, the binding was lowered to 80%. EN unformulated had a binding of 90% and properly formulated the binding was decreased to 60%. The lower binding of EN was expected to have an effect on the lag-time but, the increased rate of permeation was not expected due to the low solubility of EN.

Additionally, EN has a lower MIC (Minimum Inhibitor Concentration) compared to CPO. (1 ug/ml compared to 10 ug/ml). Calculating the time to MIC for EC compared to CPO it was found that EN formulation reach the MIC in less than 1 week where the formulated patch for CPO requires 2 weeks. (Table 6). Therefore, translating to clinic, the treatment for full cure would be decreased from a typical 9 months to 3 months.

TABLE 6

| Formulation | MIC (micrograms/ml) | Time to MIC (Days) |
|---|---|---|
| Ciclopirox Patch | 10 | 13.89 |
| PenLac | 10 | 28.56 |
| Econazole Control | 1 | 8.49 |
| Prototype H4 | 1 | 6.04 |
| Prototype P1 | 1 | 5.86 |

The enhanced permeation of EN compared to CPO was unexpected due to the low solubility of EN. EN was hypothesized to be nearly impossible to formulate because its aqueous solubility is 1.5 micrograms/ml compared to 1.4 mg/ml for ciclopirox. It is hypothesized that the decreased in keratin bind is the primary cause for the enhanced permeation. This holds promise for EN because the keratin binding for the recently approved eficonzole is 99%. (Jublia).

CONCLUSION

The Treatment of onychomycosis is challenging because the infection is embedded within the nail. This makes it difficult to reach. Thiourea is selected to be the penetration enhancer to be incorporated into the patch formulation to increase the penetration. From both skin and nail permeation study, it further more confirmed that thiourea can improve the drug penetration towards both skin and nail plate. It can directly act on the target tissues, break the disulphide bonds in keratin, open more sites for the drug to bind with. Also, the patch formulation itself offers an occlusive condition. It can help seal the water inside and hydrate the nail plate which can change the permeation of the nail. This is a big advantage compare to other nail topical formulation (for example, nail lacquer, actually dry out the nail plate instead of hydrating it).

So through combing both penetration enhancer and nail patch formulation, it produces an effective nail topical formulation to improve the penetration to the nail bed.

REFERENCES

Hydration Effect on Human Nail Permeability, by Hemali B. Gunt, Pharmaceutical sciences, University of Cincinnati. Jun. 5, 2006.

A Preformulation development study for the transungual delivery of the antifungal drug econazole nitrate by Li, Cong, M. P. S., Temple University, 2013.

Enhanced Econazole Penetration into Human Nail by 2-n-Nonyl-1,3-dioxolane. Xiao ying huil, Macrochem Corporation, 2002.

In vitro susceptibilities to ciclopirox, butenafine HCL and econazole nitrate. Kokjohn et al.

Human Nail Plate Modifications Induced by Onychomycosis: Implications for Topical Therapy. A. Baraldi & S. A. Jones & S. Guesné & M. J. Traynor & W. J. McAuley & M. B. Brown & S. Murdan. October, 2014.

Nail Penetration of Sertaconazole with a Sertaconazole-Containing Nail Patch Formulation. Rudy Susilo, 1 Hans C. Korting, 2 Wolfgang Greb3 and Uwe Phillip Strauss1. Am J Clin Dermatol 2006.

Drug Delivery Across Human Nail. Patel R P, Naik S A, Patel N A, Suthar A M. International Journal of Current Pharmaceutical Research. 2009; 1(1).

Efinaconazole Topical Solution, 10% The Development of a New Topical Treatment for Toenail Onychomycosis. Richard A. Pollak, DPM, MS*, 2014.

Baran R, Kaoukhov A. Topical antifungal drugs for the treatment of onychomycosis: an overview of current strategies for monotherapy and combination therapy. Journal of European academy of Dermatology and Venereology. 2005; 19:21-9.

Bonina F P, Montenegro L. Penetration enhancer effects on in vitro of heparin sodium percutaneous absorption salt. International Journal of Pharmaceutical Sciences. 1992; 82:171-7.

Elkeeb R, AliKhan A, Elkeeb L, Hui X, Maibach H I. Transungual drug delivery: Current status. International Journal of Pharmaceutics. 2010; 384(1-2):1-8.

H. N. Shivakumar, Vaka Sr, Madhav N V S, Chandra H, Murthy S N. Bilayered Nail Lacquer of Terbinafine Hydrochloride for Treatment of Onychomycosis. Journal of Pharmaceutical Sciences. 2010; 99:4267-76.

Gupta A K, Simpson F C. New therapeutic options for onychomycosis. Expert Opinion in Pharmacotherapy 0.2012; 13 (8):1131-42.

The disclosures of each and every patent, patent application, and publication cited herein are hereby incorporated herein by reference in their entirety.

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A medicinal patch comprising:
   a reservoir layer comprising a pharmaceutical composition comprising an imidazole class antifungal drug and a permeability enhancer; and
   a skin adhesive layer comprising an acrylate;
   wherein the reservoir layer or the skin adhesive layer further comprises polyvinylpyrrolidone;
   wherein neither the reservoir layer nor the skin adhesive layer includes a disintegrant;
   wherein the reservoir layer does not comprise a resinous crosslinking agent impregnated with the composition;
   wherein the skin adhesive layer does not comprise an imidazole class antifungal drug; and
   wherein the surface pH of the medicinal patch is between 4 and 6.

2. The medicinal patch of claim 1, wherein the imidazole class antifungal drug is econazole nitrate.

3. The medicinal patch of claim 1, wherein the permeability enhancer is thiourea.

4. The medicinal patch of claim 1, wherein the reservoir layer or the skin adhesive layers further comprises propylene glycol.

5. The medicinal patch of claim 1, wherein the reservoir layer or the skin adhesive layer further comprises a hydrophobic plasticizer.

6. The medicinal patch of claim 5, wherein the hydrophobic plasticizer comprises triethyl citrate.

7. The medical patch of claim 1, further comprising a backing membrane.

8. A method for treating a fungal infection in a subject, comprising administering to the subject the medicinal patch of claim 1.

9. The method of claim 8, wherein the fungal infection is a nail fungal infection.

10. The method of claim 8, wherein the fungal infection is onychomycosis.

11. The method of claim 8, wherein the fungal infection affects a portion of the subject' skin.

12. The method of claim 8, wherein the fungal infection affects at least one of the subject's nail.

13. A medicinal patch comprising a drug-containing reservoir and skin contact adhesive, wherein the drug-containing reservoir and skin contact adhesive are separate and distinct layers;

wherein the reservoir layer consists of a) a pharmaceutical composition consisting of an imidazole class antifungal drug and optionally one or more excipients; b) a permeability enhancer; and c) polyvinylpyrrolidone;

wherein the skin adhesive layer consists of d) an acrylate;

wherein neither the reservoir layer nor the skin adhesive layer includes a disintegrant; and wherein the surface pH of the medicinal patch is between 4 and 6.

* * * * *